(12) United States Patent
Haeffner et al.

(10) Patent No.: US 6,745,131 B2
(45) Date of Patent: Jun. 1, 2004

(54) FEEDSTUFFS AND METHODS FOR OBTAINING THEM

(75) Inventors: Jürgen Haeffner, Ingelheim (DE); Guy Harari, Atlanta, GA (US); Thomas D'Alfonso, Sceaux (FR)

(73) Assignee: Adisseo France S.A.S., Antony (FR)

(*) Notice: Subject to any disclaimer, the term of this patent is extended or adjusted under 35 U.S.C. 154(b) by 428 days.

(21) Appl. No.: 09/918,483

(22) Filed: Aug. 1, 2001

(65) Prior Publication Data

US 2002/0090442 A1 Jul. 11, 2002

Related U.S. Application Data

(63) Continuation-in-part of application No. 09/653,549, filed on Aug. 31, 2000.
(60) Provisional application No. 60/151,760, filed on Aug. 31, 1999.

(30) Foreign Application Priority Data

Apr. 14, 2000 (EP) .......................................... 001083500

(51) Int. Cl.[7] .......................... G01N 31/00; G06F 19/00
(52) U.S. Cl. ....................................................... 702/22
(58) Field of Search .............................. 702/22, 23, 27; 426/442, 53, 54, 531

(56) References Cited

U.S. PATENT DOCUMENTS

| | | | |
|---|---|---|---|
| 4,117,170 A | | 9/1978 | Washam |
| 4,211,796 A | | 7/1980 | Lanter et al. |
| 4,225,621 A | | 9/1980 | Lanter et al. |
| 4,234,604 A | | 11/1980 | Betz et al. |
| 4,311,713 A | | 1/1982 | Betz et al. |
| 4,401,680 A | | 8/1983 | Young |
| 4,705,689 A | * | 11/1987 | Tanner et al. .................. 426/2 |
| 4,786,182 A | | 11/1988 | Larsen |
| 5,085,883 A | * | 2/1992 | Garleb et al. ............... 426/590 |
| 5,531,994 A | * | 7/1996 | Schmidt et al. ............. 424/405 |
| 5,627,346 A | * | 5/1997 | Weibel et al. ................ 177/64 |
| 5,720,971 A | | 2/1998 | Beauchemin |
| 5,922,343 A | | 7/1999 | Stucker |
| 5,952,193 A | | 9/1999 | Shimamura |
| 6,070,128 A | | 5/2000 | Descales |
| 6,076,043 A | | 6/2000 | Liu |
| 6,166,382 A | | 12/2000 | Baker |
| 6,169,232 B1 | | 1/2001 | Hey |
| 6,238,709 B1 | | 5/2001 | Kalmbach |
| 6,248,939 B1 | | 6/2001 | Leto |
| 6,333,062 B1 | | 12/2001 | Fontana |

FOREIGN PATENT DOCUMENTS

| WO | WO 83/02158 | 6/1983 |
|---|---|---|
| WO | WO 89/11090 | 11/1989 |

OTHER PUBLICATIONS

Van Kempen et al., "NIRS May Provide Rapid Evaluation of Amino Acids", Feedstuffs, Dec. 2, 1996.
Van Kempen et al., "Near–Infrared Reflectance Spectroscopy in Precision Feed Formulation", J. Appl. Poultry Res. 6: 471–477 (1997).
Copy of co–pending application No. 09/918,512, filed Aug. 1, 2001.
Amino News, "Amino acid variation in compound feed: Practical relevance and means to control variability", vol. 1, No. 3, Dec. 2000.
Copy of co–pending application No. 09/653,549, filed on Aug. 31, 2000.

* cited by examiner

Primary Examiner—John Barlow
Assistant Examiner—Demetrius R. Pretlow
(74) Attorney, Agent, or Firm—Finnegan, Henderson, Farabow, Garrett & Dunner, LLP

(57) ABSTRACT

Improved feedstuffs and methods for obtaining them. One embodiment relates to the selection of a feedstuff for use in an animal feed, and enhancing batches of the feedstuff with one or more nutrients to obtain an improved feedstuff. Other embodiments of the invention relate to the improved feedstuff, an animal feed comprising the feedstuff, and a method of feeding an animal with the feedstuff. The improved feedstuff possesses consistent, desired levels of nutrients with a lower than natural variance in those levels.

34 Claims, 14 Drawing Sheets

FEEDSTUFFS AND METHODS FOR OBTAINING THEM

CROSS REFERENCE TO RELATED APPLICATIONS

This patent application is a continuation-in-part under 35 U.S.C. § 120 of co-pending U.S. patent application Ser. No. 09/653,549, filed on Aug. 31, 2000, which claims the benefit of priority under 35 U.S.C. § 119(e) to U.S. provisional application No. 60/151,760, filed on Aug. 31, 1999. This application also claims the benefit of priority under 35 U.S.C. § 119(a) to European patent application no.00 1083500, filed on Apr. 14, 2000. The contents of all priority documents are incorporated by reference herein.

FIELD OF THE INVENTION

This invention relates to improved feedstuffs and methods for obtaining them. One embodiment of the invention relates to selecting batches of a feedstuff for use in an animal feed, and enhancing the selected batches of the feedstuff with one or more nutrients to obtain an improved feedstuff. Other embodiments of the invention relate to the improved feedstuff, an animal feed comprising the feedstuff, and a method of feeding an animal with the feedstuff.

BACKGROUND

Animal feeds contain a variety of ingredients. One example poultry feed contains 50% corn, 25% soyabean meal, 20% byproducts suitable for animal feed, and 5% minerals, vitamins, supplements and other feed additives. Feed formulations for other animals may be different and, like poultry, may vary within any given animal type. Soyabean meal is one common ingredient in animal feeds, serving as a source of, for example, vegetable protein.

Control over the nutrient composition of animal feeds assists in the healthy and efficient growth of the animals. The constituent raw materials for use in animal feeds, however, often vary significantly in nutrient composition. For example, soyabean meal is classified into high protein soyabean meal (HPSBM) with 49% protein, and low protein soyabean meal (LPSBM) with 44% protein. In reality, however, neither product has a fixed level of protein. Instead, the protein level varies within certain tolerance limits about an average value among batches of the products. Soyabean meal also contains amino acids and other nutrients. Similar to the amount of protein, the amounts of amino acids, for example lysine, methionine, threonine and tryptophane, vary between different batches of soyabean meal. For instance, a coefficient of variation ("CV") of approximately 10% of lysine and methionine levels is common between batches of soyabean meal.

Variations in nutrient levels between batches of feedstuffs, such as soyabean meal, render it difficult to ensure that an animal's diet includes the desired levels of nutrients. One attempt at ensuring desired levels of nutrients in animal feed includes assessing the natural variation of the level of nutrient in batches of material, and adding a sufficient amount of supplemental nutrient to all batches to achieve a guaranteed high level of the nutrient. This technique does not reduce the natural variation in nutrient levels. Instead, it simply raises the average level of the nutrient to a higher average level. Thus, some batches of the raw material will still contain less than needed levels of nutrients. Other batches, on the other hand, will contain excess levels of nutrients, leading to extra cost and higher levels of pollution in the form of nitrogen and phosphorus in the manure of animals fed those diets.

SUMMARY OF THE INVENTION

The invention relates to improved feedstuffs and methods for obtaining them. The feedstuffs made according to the invention possess consistent, desired levels of nutrients with a lower than natural variance in those levels.

Applicants have found that certain clusters of a feedstuff can be identified, for example at a soy crusher, having nutritional profiles that make those batches favorable to feed formulation software that chooses beneficial materials for inventory and for inclusion in feed formulations at a mill. These clusters are undervalued if one only looks at the expected profile of nutrient composition rather than on actual measured values, and if one only looks at the relative proportions of nutrients with respect to the specifications among all of the feed formulas produced by the feed mill.

With reference to the clusters of batches discussed above, only minimal supplementation of desired nutrients may be necessary to reach a target nutrient composition, enough product can be manufactured from the supplemented batches to meet anticipated demand, and the value of the final product can be higher than the price of supplement and raw material. For example, total protein and total and digestible methionine and lysine can be measured in batches of soyabean meal, a cluster of those batches can be found that has relative proportions of these nutrients close to a desired value, minimal supplementation of only synthetic methionine may be needed to reach a target composition, and animal feeds using the improved feedstuff can be lower in cost, lower in variability, and higher in digestibility than that which could be obtained by conventional feed formulation with existing raw materials.

One embodiment of the invention is a method that comprises:
measuring the level of one or more nutrients in batches of a feedstuff;
determining a target nutrient composition of the feedstuff;
identifying at least one cluster of one or more batches of the feedstuff;
determining, for the at least one cluster, an amount of one or more supplemental nutrients needed by the batches in the cluster to reach the target nutrient composition; and
determining, for at the least one cluster, an economic advantage to supplementing the batches in the cluster with the one or more supplemental nutrients.

Other embodiments of the invention relate to supplementing the batches in the cluster and combining them to make an improved feedstuff. Still other embodiments of the invention cover the improved feedstuff, an animal feed comprising the improved feedstuff, and a method of feeding the animal feed to an animal. Another embodiment of the invention is a feasibility method. The feasibility method involves analyzing only a fraction of a total number of batches of feedstuff to estimate the composition of the total number of batches, and then determining from those results an economic advantage to proceed to make the improved feedstuff from a projected number of batches within the total. Another embodiment of the invention is a production method, which involves making the improved feedstuff once approved under the feasibility method.

DETAILED DESCRIPTION OF THE INVENTION

Figure 1:
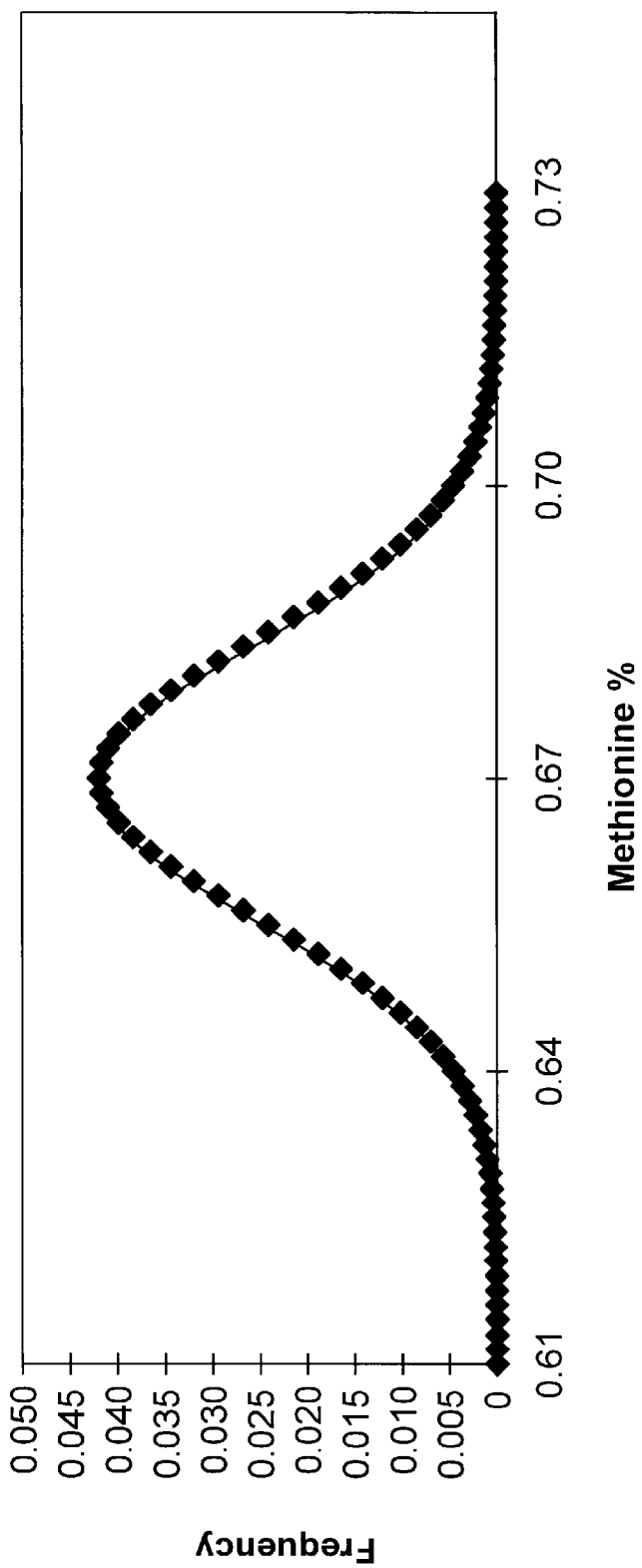
FIG. 1 visually illustrates the statistical distribution of the levels of methionine measured in batches of soyabean meal.

The invention relates to improved feedstuffs and methods for obtaining them. For example, the invention provides a method of analyzing, selecting and enhancing batches of a feedstuff in a manner that reduces the tendency to over-formulate the nutrients, while ensuring target levels of nutrients in the supplemented product. The feedstuffs made according to the invention possess consistent, desired levels of nutrients with a lower than natural variance in those levels, and have an economic advantage over known feedstuffs.

A first embodiment of the invention is a method that comprises:

measuring the level of one or more nutrients in batches of a feedstuff;

determining a target nutrient composition of the feedstuff;

identifying at least one cluster of one or more batches of the feedstuff;

determining, for the at least one cluster, an amount of one or more supplemental nutrients needed by the batches in the cluster to reach the target nutrient composition; and determining, for at the least one cluster, an economic advantage to supplementing the batches in the cluster with the one or more supplemental nutrients.

The "feedstuff" in this and other embodiments of the invention includes, for example, soyabean meal, corn, and byproducts such as bakery by-products, distillers by-products, or animal by-products. The feedstuff may also include combinations of individual feedstuffs.

The "nutrient" whose level is measured in this and other embodiments of the invention includes any substance desired for use in a feedstuff. The nutrient level may be expressed, for example, as a weight percent of the feedstuff. The nutrient can be, for example, total amino acid or acids, digestible amino acid or acids, or protein. The nutrient level may also be, for example, total, digestible, or both total and digestible amino acid or amino acids. Example amino acids include methionine, lysine, threonine, and tryptophane. The nutrient may also be fat, oil, calories, fiber, carbohydrate, a vitamin or a mineral (such as calcium and phosphorus).

The "measuring" step of this and other embodiments of the invention involves measuring the level of one or more nutrients by any suitable means. For example, the measuring step may involve measuring the levels of one or more, or two or more, or three or more, or four or more nutrients, for example, one or two or three or four nutrients.

Nutrient levels in this and other embodiments of the invention can be measured by any procedure capable of performing such measurements. For example, nutrient levels can be measured by "in vitro" analysis techniques such as near infrared reflectance spectroscopy ("NIRS"). By establishing a database relating the NIRS to the nutrient levels (measured by other means), it is possible to use the NIRS of a given batch of feedstuff to assess its nutrient content. For instance, a database can be established relating the NIRS spectrum of soyabean meal to its amino acid content, subjecting incoming batches of soyabean meal to spectroscopy, then using the database to derive the amino acid content of the incoming batches. The NIRS measurements may be carried out analogously to those described in Van Kempen and Simmins, "Near-infrared Reflectance Spectroscopy in Precision Feed Formulation," J. Appl. Poultry Res., vol. 6, pp 471–475 (1997) and Van Kempen and Jackson, "NIRS May Provide Rapid Evaluation of Amino Acids," Feedstuffs (Dec. 2, 1996). The contents of both documents cited above are incorporated by reference herein.

The NIRS method may be applied not only to amino acid content of soyabean meal, but also to other nutrient levels in other feedstuffs. For example, the caloric content, and specifically the metabolizable energy content, of corn, or the fat composition of bakery by-product meal, or the amino acid or caloric content of animal by-products, may be measured by NIRS. The digestibility of nutrient in the feedstuff can also be measured using NIRS and the appropriate comparative databases. For purposes of this invention, digestibility is the proportion of a particular nutrient actually available to the animal to metabolize. For example, available phosphorus refers to the amount of phosphorous metabolized by the animal, digestible amino acids are the amount of amino acids metabolized by the animal, and metabolizible energy is the amount of calories in the feed that are metabolized by the animal.

Figure 2:
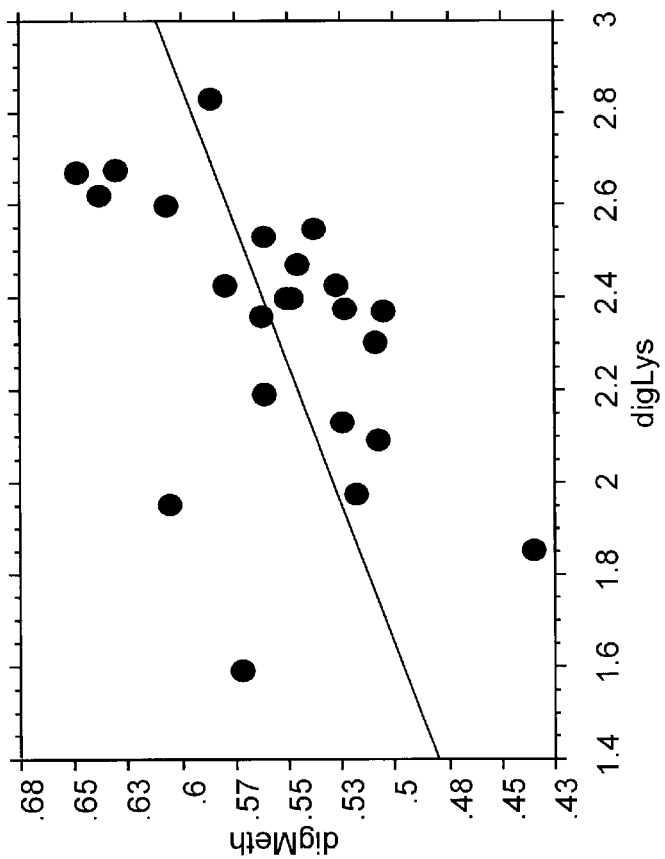
FIG. 2 visually illustrates the statistical distribution of the levels of digestible methionine and lysine measured in batches of soyabean meal.

The statistical distribution of nutrient levels between batches may also be evaluated when measuring nutrient levels in the batches. The statistical distribution, which may comprise mean values for nutrient levels and the standard deviations for those values, may be determined, for example, by a computer-based platform. Visually, the statistical distribution of one nutrient level among multiple batches may be illustrated, for example, as in FIG. 1. The X-axis of FIG. 1 represents the level of methionine in batches of soyabean meal, and the Y-axis represents the frequency of that level appearing in the batches. The statistical distribution of two nutrient levels may be illustrated, for example, as in FIG. 2. The X-axis of FIG. 2 represents the percent of digestible lysine in batches of soyabean meal, while the Y-axis represents the percent of digestible methionine in the batches. Each point in FIG. 2 represents a measurement of nutrient levels for a particular batch of feedstuff. The frequency of the levels for each nutrient may be seen visually by comparing the concentration of points between any given levels of ingredient. The statistical distribution of three or more nutrients becomes more difficult to illustrate visually, but, as with the one and two component systems, can be evaluated using a computer-based platform.

Figure 3:
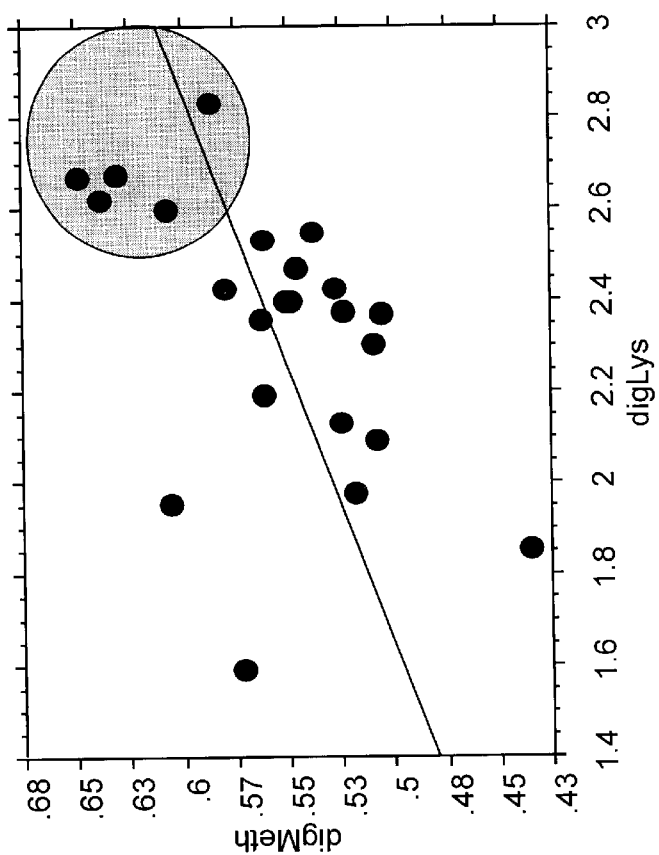
FIG. 3 visually illustrates a selected cluster of batches, encircled within the shaded area of the Figure.

A "batch" of feedstuff in this and other embodiments of the invention is a certain quantity of the feedstuff. A batch of feedstuff may be quantifiable by, for example, a mass or volume measurement. A "cluster" of batches of the feedstuff is a grouping of one or more batches of the feedstuff. The cluster contains from one batch to any number of batches less than the total number whose nutrient levels are measured. The individual batches in a cluster may contain the same quantity of feedstuff, or may differ in quantities of feedstuff. As an example, any batches falling within the shaded circle in FIG. 3 may constitute a "cluster" of batches. The batches falling within that circle comprise similar digestible methionine and lysine contents, as indicated by their position visually in the Figure. A cluster may also be defined visually by other shapes other than a circle. For example, a cluster may be represented visually by an ellipse, or by an unsymmetrical shape.

A cluster is not limited to groupings of batches similar in composition. Instead, a cluster of batches includes any grouping of batches, regardless of similarities in their compositions. Thus, a cluster of batches could include in FIG. 3, for example, one or more batches having high digestible lysine contents and low digestible methionine contents, grouped with one or more batches having low digestible lysine contents and high digestible methionine contents.

The first "determining" step in this and other embodiments of the invention involves determining a target nutrient composition of the feedstuff. The target nutrient composition may include, for example, a nutrient composition desired for a feedstuff to be used in a particular animal diet. The target nutrient composition may include threshold minimum levels of one or more nutrients or desired ranges of one or more nutrient levels.

The second "determining" step in this and other embodiments of the invention involves determining, for at least one cluster of batches, the amount of one or more supplemental nutrients needed by the batches in the cluster to reach the target nutrient composition. The amount of supplemental nutrient or nutrients needed by batches within any selected cluster may be determined, for example, by observing from the measurement step the amounts of the relevant nutrients in the batches, and determining the remaining amounts needed to reach the target nutrient composition.

The third "determining" step in this and other embodiments of the invention involves determining, for the at least one cluster, an economic advantage to supplementing the batches in the cluster with the one or more supplemental nutrients. The determination of economic advantage to supplementing the batches involves determining that the economic value of obtaining the resulting product outweighs the value of processing the feedstuff in a conventional manner. The economic advantage may take the form of, for example, an expected higher profit to the manufacturer and/or seller of the improved feedstuff, a savings to a customer when purchasing the improved feedstuff or when purchasing an animal feed containing the feedstuff, or all of the above.

The economic value of the improved feedstuff can be measured, for instance, by comparing its expected use in the market compared to feedstuffs made according to conventional methods. Batches of feedstuff within a given cluster, supplemented with appropriate amounts of nutrients, can possess more reliable minimum levels of desired nutrients and lower variability in those nutrient levels between batches. Those features render the improved feedstuff more competitive with known feedstuffs, and more favorable for use in animal feeds compared to known feedstuffs. Feed formulation software, such as "Brill" marketed by Brill Corporation, tend to select the improved feedstuffs for use in animal feed over other known feedstuffs. That estimated demand for a feedstuff according to the invention, calculated for example using feed formulation software, can allow for a prediction of expected sales of the improved product and a determination that there is an ultimate economic advantage to making the improved feedstuff rather than processing the feedstuff according to conventional methods. The ultimate economic advantage can take the form of, for example, a higher profit to the manufacturer relative to what could have been earned by processing the feedstuff in a conventional manner.

The ultimate determination of an economic advantage to supplementing the batches in the cluster may also involve evaluating the cost of such supplementing and any other cost involved in making the improved feedstuff. The cost of supplementing the batches includes, for example, the cost of the needed supplemental nutrients, and the cost of equipment, time and labor to perform the supplementing. The cost of the process may also include any costs for separating the supplemented batches from all other batches, and combining the batches to make the improved feedstuff.

Implicit in the determination of economic value of the improved feedstuff and the cost of supplementing the feedstuff is a consideration of the quantity of the feedstuff within the selected cluster, and not only the nutritional composition of the batches. For example, a determination of expected use of the feedstuff in the market, based on predictions made using feed formulation software, will involve as one factor whether sufficient quantities of the feedstuff can be made to satisfy demand for the product. As another example, the cost of supplementing the batches and making the feedstuff may also depend on the quantity of feedstuff to be supplemented and made.

The determination of an economic advantage may also take into account any effect on the value of feedstuff that remains once separated from the supplemented feedstuff. For example, removal and separation of batches of product having highly desirable nutrient contents may de-value the feedstuff that remains. This effect may be minimized by separating and supplementing, for example, a small percentage, for example 5% or less, of the total number of batches analyzed. In one example of the invention, a small enough quantity of nutrient-rich batches to be supplemented are removed so that the nutrient composition of the remaining bulk of the feedstuff is not affected in a statistically significant manner.

The determination of economic advantage discussed above may be performed using a computer-based platform, for example using a Monte-Carlo simulation. Information useful in the computer calculation can include the price and amounts of the supplemental nutrient or nutrients, the cost of performing the supplementing steps, and data relating to market sensitivity of animal feed or feedstuff price to nutrient composition levels and variability of nutrient composition levels. The calculation may also include information on the quantity of supplemented feedstuff to be produced, as well as market demand for a lower quantity of higher-value feedstuff compared to a higher quantity of lower-value feedstuff.

When an economic advantage is determined for supplementing the batches of feedstuff within the selected cluster, the batches may be separated from other batches, supplemented with the determined levels of supplemental nutrients, and combined to make the improved feedstuff.

The first and other embodiments of the invention may be performed in the order of steps discussed or, alternatively, in a different order where possible. For example, determination of a target feedstuff composition may precede measuring the level of one or more nutrients in the batches of the feedstuff. As another example, the supplementing of batches with the determined amount of nutrient or nutrients may be performed before or after separating the batches to be supplemented from other batches. The steps in the first and other embodiments of the invention may also be performed by evaluating, for example, the economic value of individual batches, and then identifying a cluster of batches from that evaluation that, when supplemented, will offer an economic advantage. As a visual example, the digestible lysine and methionine levels in a feedstuff may be plotted on x and y axes as shown in FIG. 2. A third axis (z-axis) may be added to represent the economic value of the batches. Clusters of batches may appear as, for example, peaks or ridges in the z-axis over the digestible lysine and methionine values, leading to an identification of the clusters for use in the invention. Such an example may be graphically represented by a contour plot, available in many statistical software packages.

As one example of the first embodiment of the invention, the total methionine and lysine, digestible methionine and lysine, and total protein in batches of soyabean meal are measured using NIRS, and a computer records the distribution of those nutrient compositions. Clusters of the batches are found having relative proportions of the nutrients close to a pre-determined threshold value derived from a minimum desired level of the nutrients in a target composition. The determination of economic advantage is made with the assistance of a data processing device, such as a programmed computer using feed formulation software. Minimal supplementation of only synthetic methionine is needed, a nutrient supplement supply device performs the supplementing step, and the supplemented batches are separated and combined to form an improved feedstuff. Diets formulated with this enhanced product are lower in cost, lower in variability, and higher in digestibility than that which could be obtained by conventional feed formulation with existing raw materials.

The method described above allows for the iterative process of selecting a cluster of batches, performing the remaining steps, and, if no economic advantage is found for supplementing the selected cluster of batches, iteratively selecting further clusters for analysis until a solution is found. Such calculations can be performed routinely by a computer. The process may also be performed with reference to one or more nutrient levels, and, if no economic advantage is found for supplementing the selected cluster of batches with those nutrients, iteratively performing the process with reference to other nutrients, or combinations of multiple nutrients until a solution is found for any selected cluster of batches. Those calculations may also be performed routinely by a computer-based platform.

The invention also includes, but is not limited to, a method for finding the optimum economic advantage based on the cluster analysis described above. For example, a selection of a cluster may result in an economic advantage being found for supplementing the cluster with the appropriate amount of supplemental nutrients and producing the improved feedstuff. Other clusters of, for example different batches, may also be found for which there would also be an economic advantage to supplementing the batches and producing the improved feedstuff. The invention covers each of those scenarios. In another embodiment, the invention also includes an iterative determination of one or more cluster analyses that identify an economic advantage to supplementing the batches in the cluster to produce the improved feedstuff, and identifying the optimum cluster selection that provides the greatest economic advantage.

The feedstuff made from the supplemented batches possesses consistent, desired levels of nutrients with a lower than natural variance in those levels, and has an economic advantage over known feedstuffs. The coefficient of variance for a given nutrient, for example one that has been supplemented in the feedstuff, can be, as low as 5%, 4% or 3%. The variance may also be lower than 3%, but is limited to the measurement of error of the measuring device (for example NIRS) and the variance of mechanical processes such as separating, weighing and mixing. The levels of nutrient in the improved feedstuff may also be more digestible to the animal. The more accurate levels of desired nutrients in the feedstuff can reduce pollution in the form of wasted nutrient in the manure of animals feed the feedstuff. This improved feedstuff constitutes a second embodiment of the invention, made by the method of:

measuring the level of one or more nutrients in batches of a feedstuff;

determining a target nutrient composition of the feedstuff;

identifying at least one cluster of one or more batches of the feedstuff;

determining, for the at least one cluster, an amount of one or more supplemental nutrients needed by the batches in the cluster to reach the target nutrient composition;

determining, for the at least one cluster, an economic advantage to supplementing the batches in the cluster with the one or more supplemental nutrients;

separating the batches in the at least one cluster from batches not in the cluster and combining them; and supplementing the batches in the at least one cluster with the one or more supplemental nutrients to obtain the improved feedstuff.

As with the first embodiment of the invention, the method steps may be performed in the order described above or in any other possible order.

A third embodiment of the invention is an animal feed, which comprises the improved feedstuff. The coefficient of variance for a given nutrient in the animal feed, for example one that has been supplemented in the feedstuff, may be, for example, as low as 6%, 5%, 4% or 3%. A fourth embodiment of the invention is a method of feeding an animal, which comprises feeding the animal the animal feed comprising the improved feedstuff. The animal may be, for example, a cow, a chicken, a pig, or a sheep.

A fifth embodiment of the invention is a feasibility method, which comprises:

measuring the level of one or more nutrients in a fraction of a total number of batches of a feedstuff;

determining a target nutrient composition of the feedstuff;

identifying at least one cluster of one or more batches of the feedstuff;

determining at least one projected number of batches, within the total number of batches, expected to fall within the at least one cluster;

determining, for the at least one projected number of batches, the amount of one or more supplemental nutrients needed by the batches to reach the target nutrient composition; and determining, for at the least one projected number of batches, an economic advantage to supplementing the batches with the one or more supplemental nutrients.

This fifth embodiment of the invention essentially performs the role of the first embodiment of the invention, but analyzing only a fraction of the number of batches of feedstuff to estimate the composition of the total number of batches, and then performing the remaining steps based on a projected composition and amount of total feedstuff available. The more representative the nutritional compositions of the fraction of batches is of the total number of batches, the more accurate the method. For example, this embodiment may involve analyzing 10% of a large number of total batches, and performing the remaining steps based on a projection that the total number of batches have a similar nutritional profile to the 10% already analyzed.

The determination of an economic advantage may take into consideration, for example, market conditions that may change between when the feasibility method is performed and when the selected batches of feedstuff will ultimately be separated and supplemented. For example, the determination of economic advantage may be a function of the relevant supplement price, or a function of market demand for particular feedstuffs, or a function of the quality or quantity of any pre-existing feedstuff already selected to be supplemented and used in an improved feedstuff. Each of these factors may be considered as a random variable in the determination of economic advantage.

As with the first embodiment of the invention, it is possible that no cluster exists that yields an economically advantageous option, for example, because the cluster is too small to be practically feasible. Also as with the first embodiment, the economics of supplementing the batches can consider the cost of analysis and supplementation, the quantity of batches selected, and the value of the enhanced feedstuff in formulation of typical animal feeds that would contain this enhanced feedstuff. As with the first embodiment of the invention, the value of the feedstuff in animal feeds may be estimated using a linear program that minimizes the cost of the animal feed while meeting the nutrient requirements.

A sixth embodiment of the invention involves a production method that comprises:

performing the feasibility method;

measuring the nutritional composition of batches of feedstuff within the total number of batches;

rejecting any batches that would not fall within the at least one projected number of batches;

accepting any batches that would fall within the at least one projected number of batches;

separating the accepted batches from the rejected batches and combining the accepted batches; and supplementing the accepted batches with the determined supplemental nutrient amount.

This production method incorporates the feasibility method, then analyzes the batches of feedstuff to accept and supplement the appropriate batches and to reject the others. Moreover, as explained above, any change in, for example, supplement price from the time of the feasibility method, may affect the scope of batches to be ultimately accepted at any point in time under this production method.

The invention will be further described by way of examples with reference to further drawings.

EXAMPLE 1

Application of Method to Batches of Soyabean Meal

Figure 4:
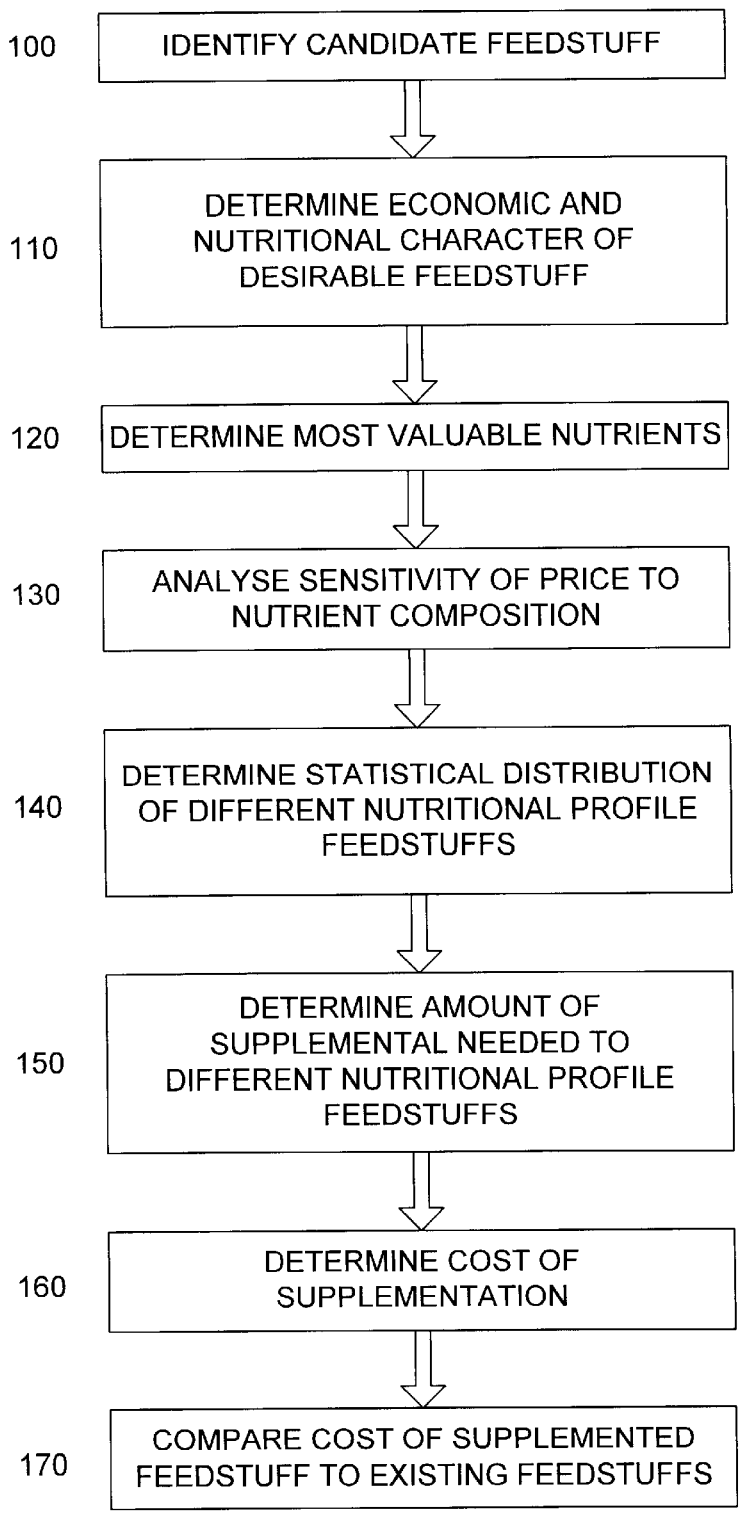
FIG. 4 illustrates a flow diagram showing an overall decision making flow in an embodiment of the invention.

FIG. 4 illustrates an overall decision flow of an example of the first embodiment of the invention. This example involves an analysis of nutrient composition in batches of soyabean meal.

Figure 5:
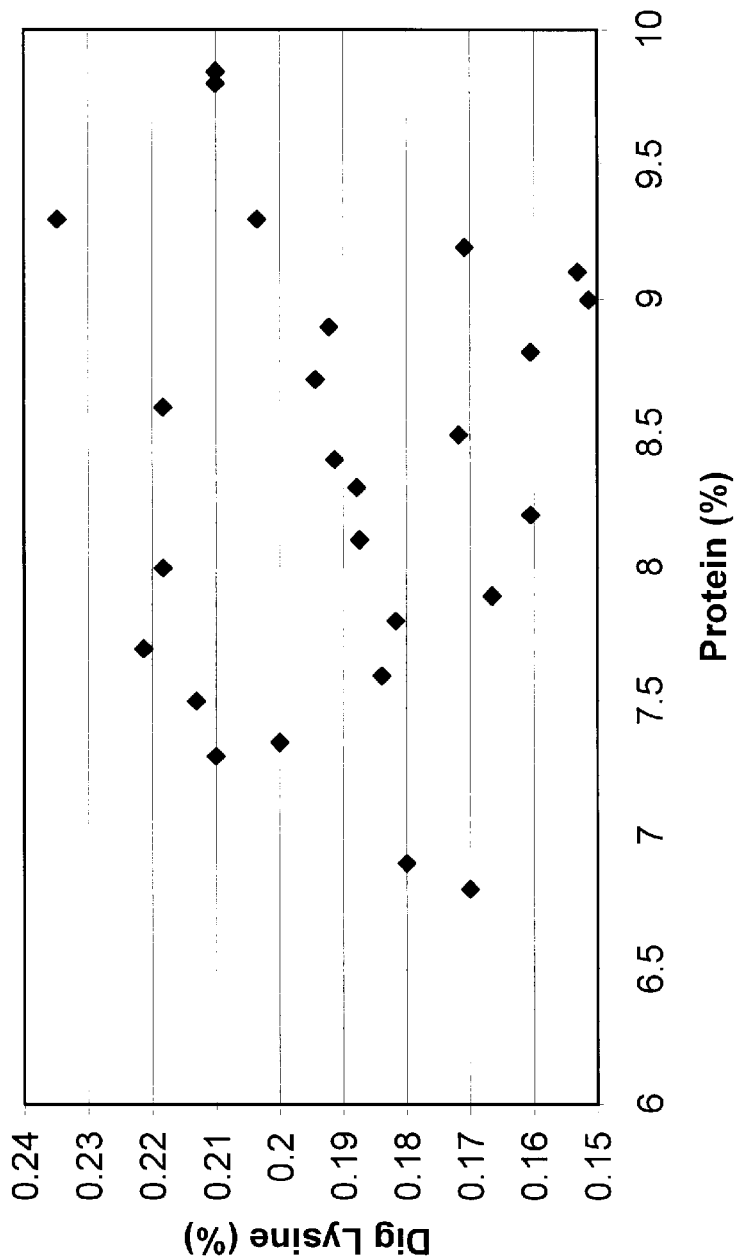
FIG. 5 illustrates the variability in digestible lysine content as a function of the protein content of randomly selected batches of corn.

The first step 100 in FIG. 4 identifies a candidate feedstuff. Example feedstuffs include soyabean meal, corn, or byproducts, such as bakery by-products, distillers by-products, or animal by-products. These feedstuffs can provide protein and other nutrients, such as amino acids, to the animal. However, the feedstuffs do not have a consistent content. FIG. 5 illustrates, in an example case of corn, the variability in digestible lysine content as a function of the protein content of randomly selected batches. The Figure reflects a widely varying digestible lysine content for any given level of protein.

The next step 110 in FIG. 4 determines the nutritional characteristics and economic characteristics (primarily acceptable price) of a desirable or ideal feedstuff. In the case of soyabean meal used for poultry feed, the soyabean meal is available basically as a high protein product (49%) or a low protein product (44%). The high protein product is more expensive at $160 per ton than the low protein product at $150 per ton. While the high protein product may be expected to have high levels of amino acid, in fact, there is a high variability in the amino acid level in both types of soyabean meal. Thus, even use of the high protein product cannot guarantee that the final feedstuff is of optimal value to the animal. Further, there is a difficult balance to be struck between the use of lower quantities of the more expensive high protein meal, or higher quantities of the lower protein cheaper soyabean meal.

The next step 120 in FIG. 4 identifies the most valuable nutrients in the feedstuff. In the case of soyabean meal, these can be, for example, methionine and lysine. Not all of the nutrient present, however, may be digestible to the animal. Thus, the total composition and the digestibility of the nutrients may be considered. In this example, it can be desirable to have a digestibility of approximately 90%, as determined by NIRS screening. The next step 130 in FIG. 4 analyzes the sensitivity of the feedstuff price to the nutrient composition. In the case of soyabean meal, it can be desirable to have the methionine and lysine content identical, if possible, with high protein soyabean meal.

The next step 140 in FIG. 4 considers whether there is sufficient feedstuff available that can be economically enhanced with supplemental nutrient to satisfy the desired nutritional profile, and thus a statistical analysis of the feedstuff is made. In the case of soyabean meal, it is found that the nutrient composition, particularly in terms of amino acid content is not uniformly distributed. Instead, the batches cluster in terms of their amino acid content. Clusters can be identified of batches of low protein soyabean meal that, despite being low in protein, are high in both total and digestible composition of amino acid. These batches require only a small amount of supplementation to achieve the desired nutritional profile; namely an amino acid profile identical to that of high protein soyabean meal.

With regard to the statistical distribution of the feedstuff, the amount of supplementation needed for each of the batches in the selected clusters is determined in step 150 in FIG. 4. This can be done by using a Monte Carlo simulation to determine the amount of supplementation needed on average and the distribution of that supplementation (minimum and maximum supplementation needed). In the case of soyabean meal, the clusters of low protein soya bean meal that are close to the high protein soyabean meal in terms of amino acid content are selected such that the minimum supplementation of methionine and lysine needed is 0% and the maximum 0.1%. In step 160, the cost of such supplementation, in terms of the raw material cost (for LPSBM this is $150 per ton), the cost of the supplement and the cost of the monitoring, analysis and supplementing equipment, is determined.

Step 170 of FIG. 4 compares the cost of producing the supplemented feedstuff to the cost of existing competing feedstuff, such as HPSBM. Table 1 below illustrates the nutrient composition and economic value of soyabean meal in the case of LPSBM, HPSBM and the enhanced product, marked as guaranteed soyabean meal (GSBM). The price of LPSBM as $150 per ton, the price of HPSBM as $160 per ton, and the price of GSBM at a selling price of $157.50 per ton still results in a reduced feed cost compared to the use of HPSBM. This is despite the fact that the cost of the additive needed is $1.60 per ton and the estimated cost of the equipment for screening the product and adding the additive is $0.75 per ton. Table 1 thus demonstrates that, using the procedure illustrated in FIG. 4, it is possible to select and enhance a raw material for a feedstuff in a manner that improves the nutritional value, while maintaining economic advantage for the user of the feedstuff.

As can be seen in Table 1, the variance in nutrient content is also significantly reduced in a mixed feed containing the GSBM product, even compared to HPSBM. The variance in nutrient content of the mixed feed using LPSBM is 4.56%, in the case of HPSBM it is 4.25%, but in the case of GSBM it is only 3.4%. Thus, even though the mixed feed in this example had a fair consistency (variance of 4.25% or 4.5%), addition of GSBM to the mixed feed reduced that variance by 20%.

TABLE 1

Nutrient composition and economic value of soyabean meal with example feedstuff of the invention

| | LPSBM | HPSBM | GSBM | |
|---|---|---|---|---|
| Ingredients | | | | |
| Protein | 44% | 49% | 44% | (same as Soy 44%) |
| Lysine | 2.74% | 3.07% | 3.07% | (same as Soy 49%) |
| Methionine | 0.60% | 0.68% | 0.68% | (same as Soy 49%) |
| TSAA | 1.23% | 1.39% | 1.35% | |
| Threonine | 1.72% | 1.94% | 1.83% | |
| Metabolizable Energy | 2244 | 2420 | 2244 | (same as Soy 44%) |
| Other Nutrients Composition/costs | X | Y | X | (same as Soy 44%) |
| Added methionine | 0% | 0% | 0.08% | (supplement used) |
| Raw Material Cost Economics | 150.00 | 160.00 | 151.63 | |
| Selling price ($/ton) | 150.00 | 160.00 | 157.50 | |
| Net value added ($/ton) | | | $5.87 | |
| A) Feed Price | 145.75 | 145.50 | A) 145.00 | |
| B) Difference | | | B) −0,50 | (lower feed cost) |
| A) Nutrient variance | 4.56% | 4.25% | A) 3.40% | |
| B) Difference | | | B) −20% | (reduced nutrient variation) |

EXAMPLE 2

Example Economic Advantage of Improved Feedstuff

As another example of the first embodiment of the invention, a cluster of batches of soyabean meal were selected having the levels of digestible methionine and lysine indicated in Table 2:

TABLE 2

Composition of batches within selected cluster of soyabean meal

| | Digestible Lysine | Digestible Methionine |
|---|---|---|
| Average % | 2.43 | 0.55 |
| Std. Dev. % | 0.09 | 0.03 |
| CV % | 3.8 | 4.8 |

Guaranteed levels of 2.25% digestible lysine and 0.6% digestible lysine were targeted, and an economic analysis was made to evaluate the feasibility of supplementing the batches with sufficient digestible methionine to reach the guaranteed level of 0.6%. Random variables in the Monte Carlo simulation included the amount of digestible methionine in the existing batches (varying according to a normal distribution with a standard deviation of 0.03%), and the cost per ton of necessary supplemental methionine (varying around $2000 per ton). The simulation was performed using 10,000 batches of soyabean meal, with each differing with respect to the random variables.

Figure 6:
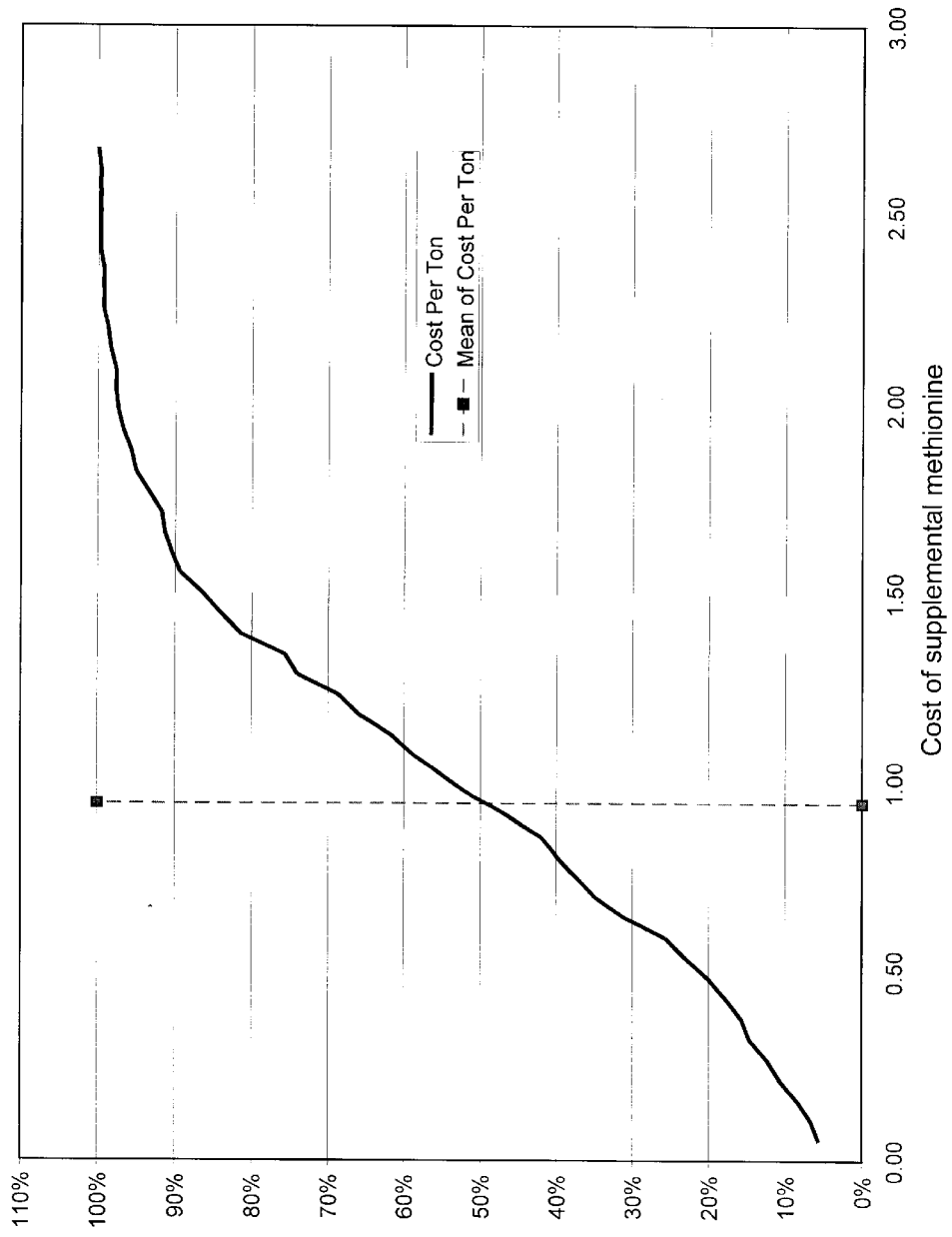
FIG. 6 illustrates a simulation-based prediction of the cost of supplemental methionine per ton of soyabean meal to be produced for a selected cluster of batches.

FIG. 6 illustrates the simulation-based prediction of the cost of supplemental methionine per ton of soyabean meal to be produced. The mean cost per ton, as indicated by the dotted line in the Figure, was calculated as $0.946/ton of soyabean meal produced. As can also be seen from the Figure, the cost of supplemental methionine is predicted to be less than $2.00 per ton of soyabean meal produced about 98% of the time.

The overall feasibility of supplementing the batches of soyabean meal with methionine as proposed, and using those batches in an animal feed, was then studied, taking into account the price of feed containing the soyabean meal to be charged to the customer, the anticipated profit, and anticipated savings to the customer. Table 3 below indicates results of the calculation using prices of the improved feedstuff GSBM from $5.00 to $7.50 higher than convention low-protein soyabean meal LPSBM. The Table indicates an expected profit on the sale of the soyabean meal, as well as a minimum customer savings in purchasing the animal feed containing the feedstuff.

TABLE 3

Economic Evaluation

| GSBM Price | $/ton profit | $/ton Minimum Customer Value |
|---|---|---|
| +$7.50 | 5.25 | 0.10 |
| +$7.00 | 4.75 | 0.20 |
| +$6.00 | 3.75 | 0.50 |
| +$5.00 | 2.75 | 0.80 |

Profit was calculated based on an expected supplemental methionine cost of less than $2.00 per ton, as well as an estimated $0.25 per ton for mechanical system costs, software, sensors etc., amortized over 5 years and 1 million tons of soyabean meal.

The minimum customer value in Table 3, meaning $/ton in reduced animal feed price, was derived from a sensitivity analysis simulating 128 feed formulas over a range of ingredient prices and nutrient specifications. Such an analysis can be performed, for example, using the "Insight" add-on to a Microsoft Excel document. The sensitivity analysis was conducted using a soyabean meal under three basic feed specifications: starter, grower, and finisher. The analysis evaluated four variations of nutrient requirements for each feed type, and two price scenarios: high prices and low prices. That analysis produced 4×4×4×2=128 diets. Table 4 illustrates the numerical results of that calculation in terms of the price per ton of the feedstuff, the percentage of soyabean meal used in the feed, the net value of the soyabean meal, and the feed cost to the customer for each of LPSBM, HPSBM and GSBM.

TABLE 4

Economic Evaluation (Cont.)

|  | Price ($/ton) | Amount (%) | Net Value ($/ton) | Net Value vs. GSBM | Feed Cost ($/ton) |
|---|---|---|---|---|---|
| LPSBM | 145.86 | 23.88 | 34.83 | −1.69 | 121.93 |
|  | 150.00 | 22.92 | 34.38 |  |  |
|  | 166.31 | 21.94 | 36.49 |  |  |
| HPSBM | 152.35 | 24.87 | 37.89 | −5.00 | 122.06 |
|  | 160.00 | 19.42 | 31.06 |  |  |
|  | 176.50 | 19.00 | 33.54 |  |  |
| GSBM | 151.98 | 24.34 | 36.99 | N/A | 121.84 |
|  | 157.50 | 22.90 | 36.07 |  |  |
|  | 172.45 | 21.91 | 37.78 |  |  |

Figure 7:
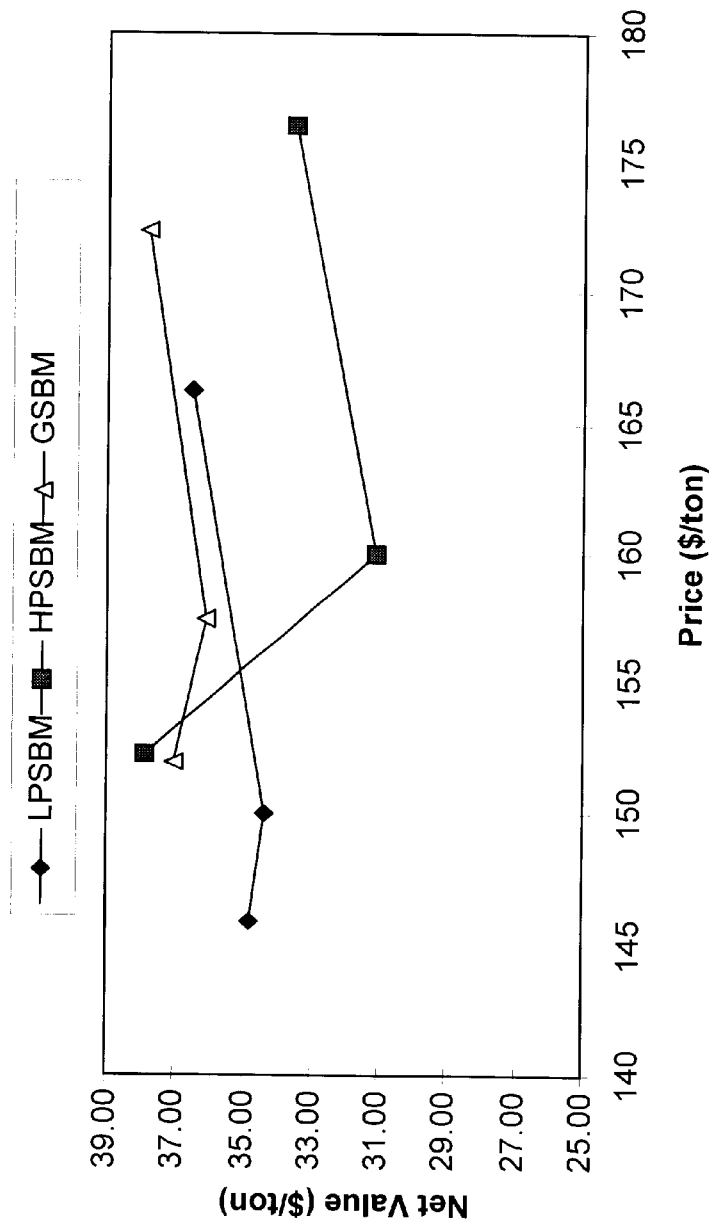
FIG. 7 illustrates an economic comparison between a feedstuff of the invention and two conventional feedstuffs.
Figure 8:
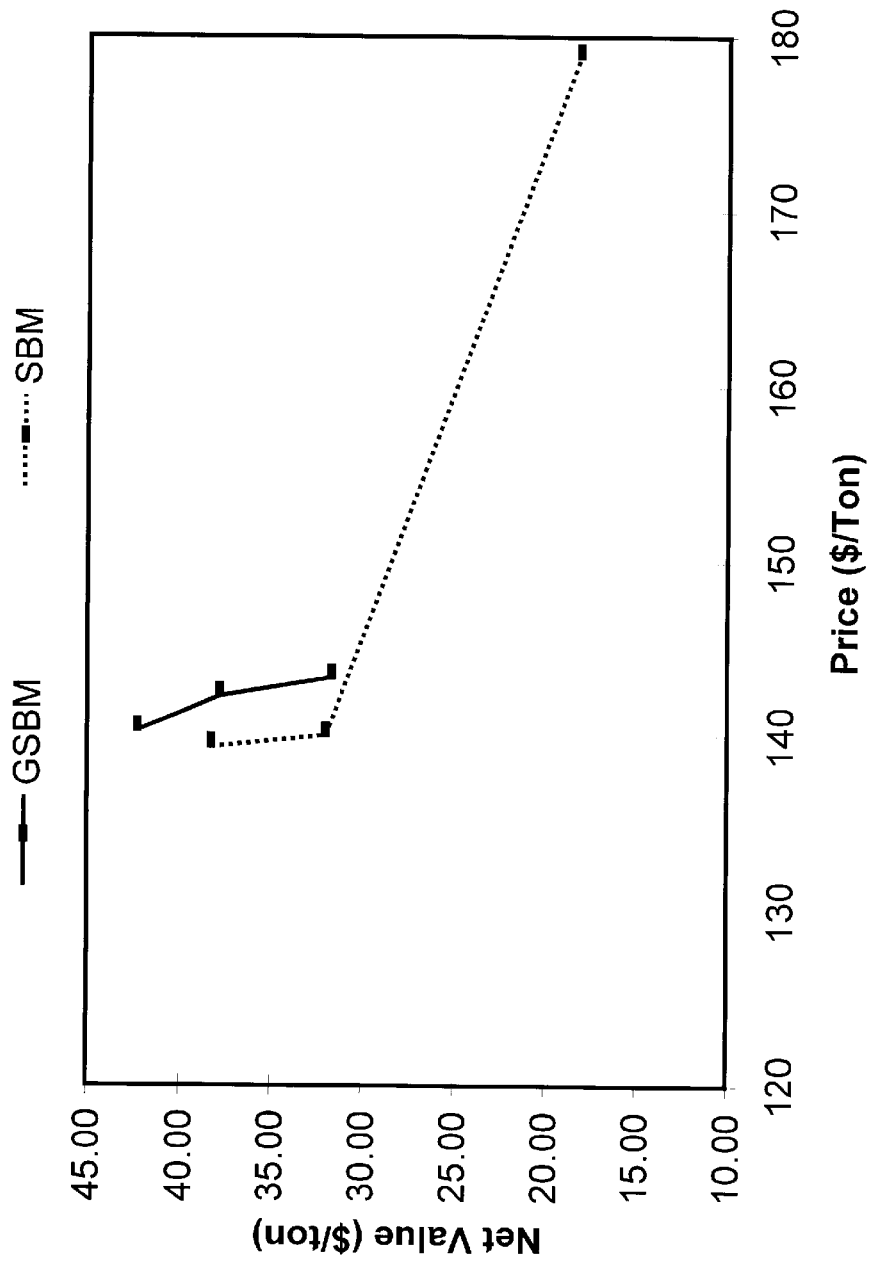
FIG. 8 illustrates an economic comparison between a feedstuff of the invention and a conventional feedstuff.

FIG. 7 visually illustrates the data of Table 4 for LPSBM and HPSBM and GSBM. As can be seen from the Figure, GSBM can be priced $7.50 per ton higher than LPSBM, $2.50 less than HPSBM, and can be more profitable than both types over a wide range of prices. Furthermore, the customer can save a minimum of $0.1/ton of feedstuff using the feedstuff of the invention compared to the conventional feedstuffs. In one embodiment, the determination of an economic advantage favors cases where profitability is higher over a range of prices as wide as the market price variation of feedstuffs that would be replaced by the enhanced feedstuff. The invention is not necessarily limited, however, to clusters of batches that offer profitability over such a wide range of prices. For example, in other circumstances, a cluster of batches may be selected having profitability over a narrower range of soyabean meal prices as illustrated in FIG. 8.

EXAMPLE 3

Application of Method to Batches of Corn

As another example of the first embodiment of the invention, batches of corn may be analyzed for caloric content. The amount of calories in corn that is digestible and metabolized by the animal is commonly referred to as "metabolizable energy" (ME). Following the procedure of FIG. 4:

Corn is identified as the feedstuff;
Clusters of corn batches with high ME and low cost are discovered;
Sufficient batches of high ME corn exist for the market;
Threshold values of metabolizable energy composition are determined;
Supplemented energy in the form of vegetable oil may be used; and
The net economic value of this new feedstuff can be determined to find an economic advantage to supplementing the batches.

EXAMPLE 4

Improved Feedstuff

Figure 9:
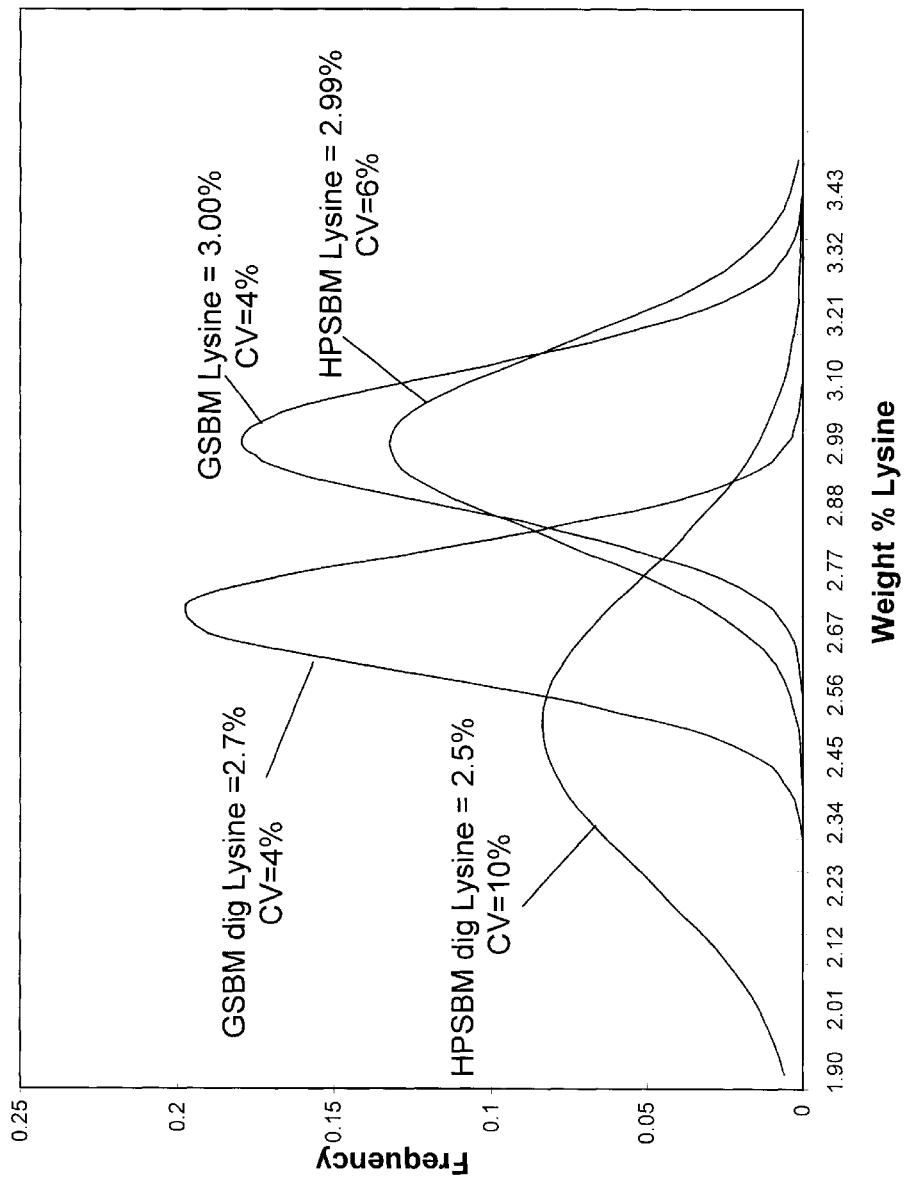
FIG. 9 illustrates levels of lysine and digestible lysine levels in an embodiment of the invention compared to a commercial feedstuff.

FIG. 9 illustrates a comparison of levels of lysine and digestible lysine levels in a feedstuff of the invention compared to a commercial feedstuff. The Figure illustrates a favorable 3.0% of lysine with CV=4% in the improved feedstuff, compared to SBM49 having lysine at 2.99% and CV=6%. The improved feedstuff is likewise more favorable in digestible lysine, showing 2.7% with CV=4% compared to SBM49 digestible lysine at 2.5% and CV=10%. Thus, the feedstuff manufacturer can use the improved feedstuff without systematic over-formulation, while confidently providing a feedstuff of guaranteed value to the animal.

The improved feedstuff of the invention is of value in that it has a desired nutritional profile, with lower than natural variance, while being available in sufficient amounts and value that is acceptable to feedstuff users. In the particular example of soyabean meal, there is an additional advantage in that the product can have a low protein content, yet high amino acid content. The low protein content is effective in reducing the environmental pollution produced by animals consuming the final feed product. The invention makes it possible to produce such a product by selecting the raw material with reference to the nutritional content so avoiding systematic over-formulation. Further, statistical analysis of the frequency distribution of the nutritional content among batches of the feedstuff allows the optimization of the selection of the raw material having regard to the amount of product to be produced, its cost of production, and the desired nutritional profile.

EXAMPLE 5

Production Method

Figure 10:
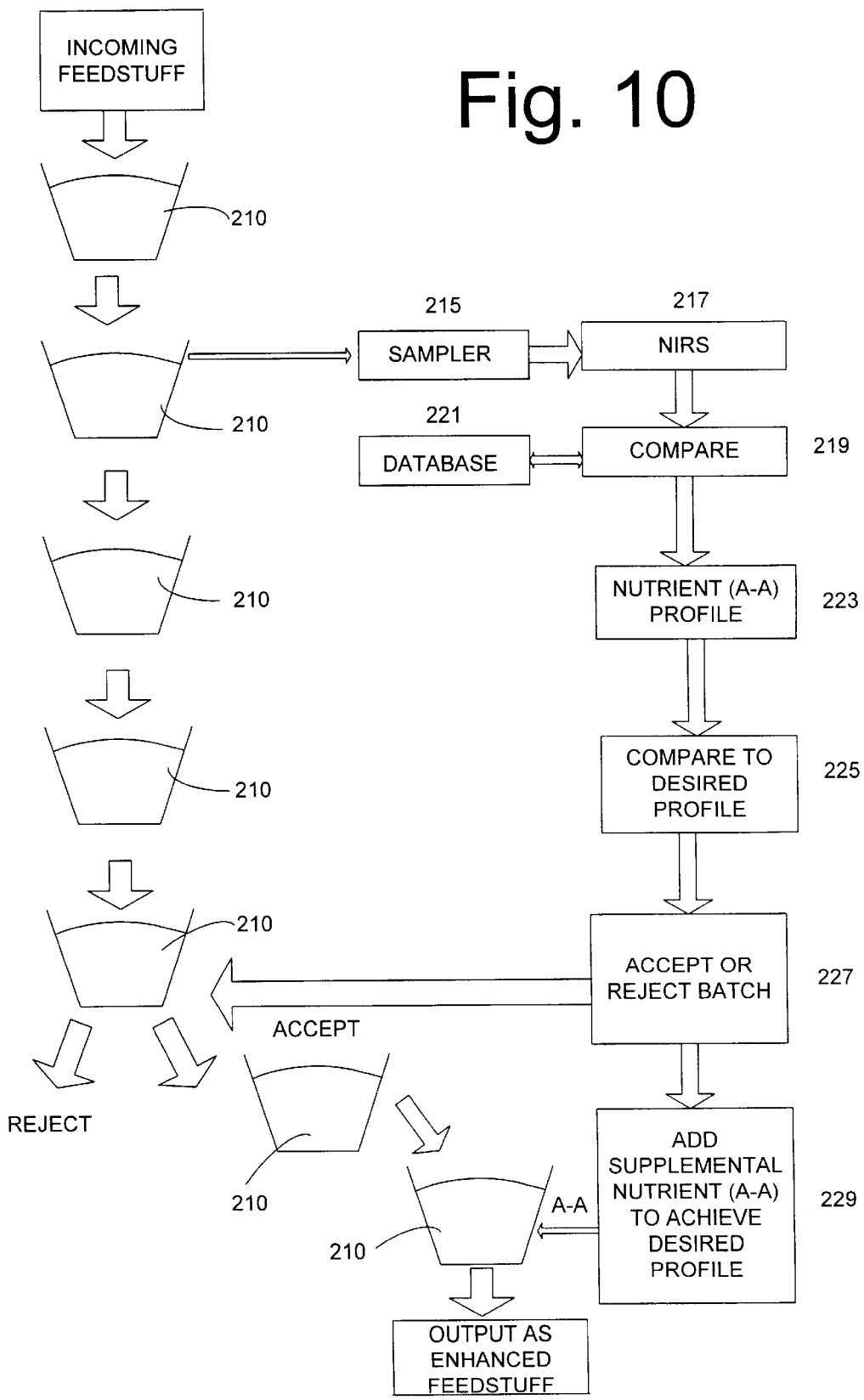
FIG. 10 illustrates schematically an example of a production method of an improved soyabean meal.
Figure 11:
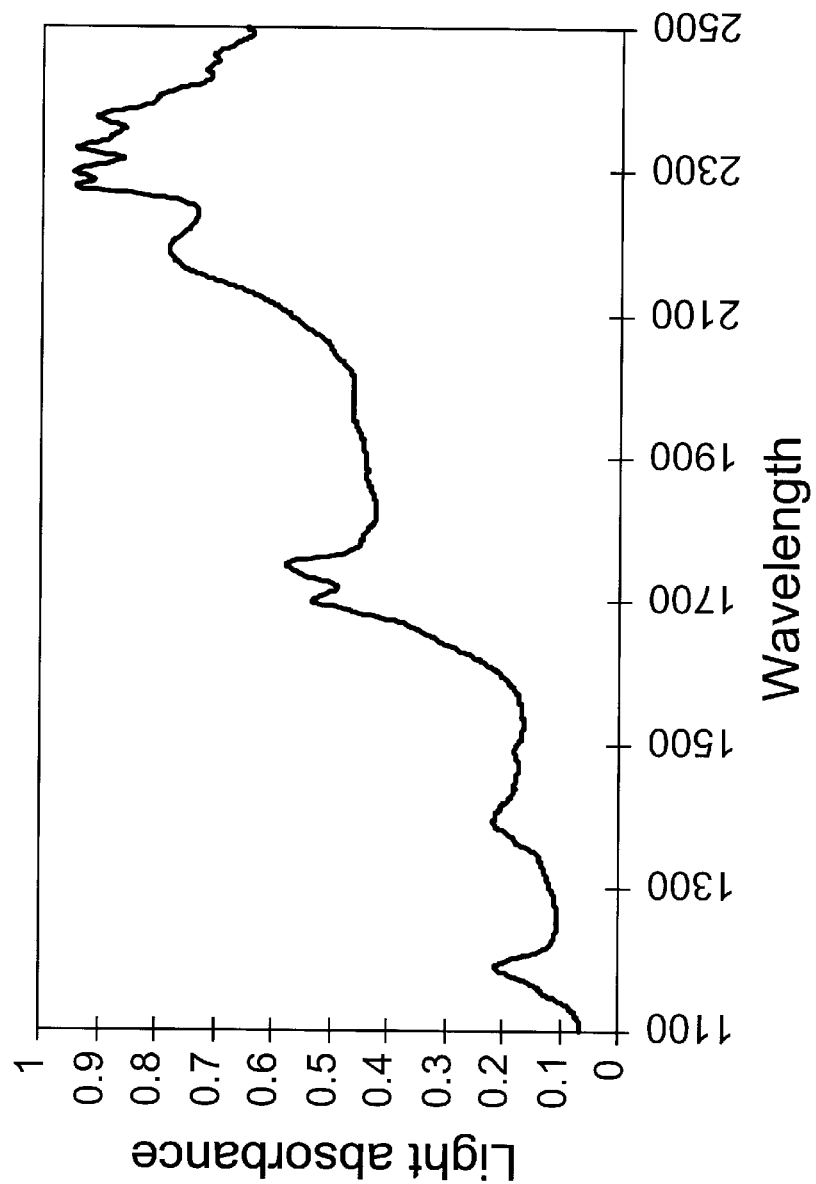
FIG. 11 illustrates an NIRS spectrum of methionine.

FIG. 10 illustrates schematically an example of the production method of an enhanced soyabean meal. Batches of soyabean meal 210 are sampled by a sampler 215 and subjected to near infrared reflectance spectroscopy by spectrometer 217. The spectrum is compared at 219 to spectra stored in a database 221 relating the spectra to the amino acid content. FIG. 11 illustrates the NIRS spectrum of methionine and FIG. 12 illustrates the NIRS spectrum of soyabean meal.

Figure 12:
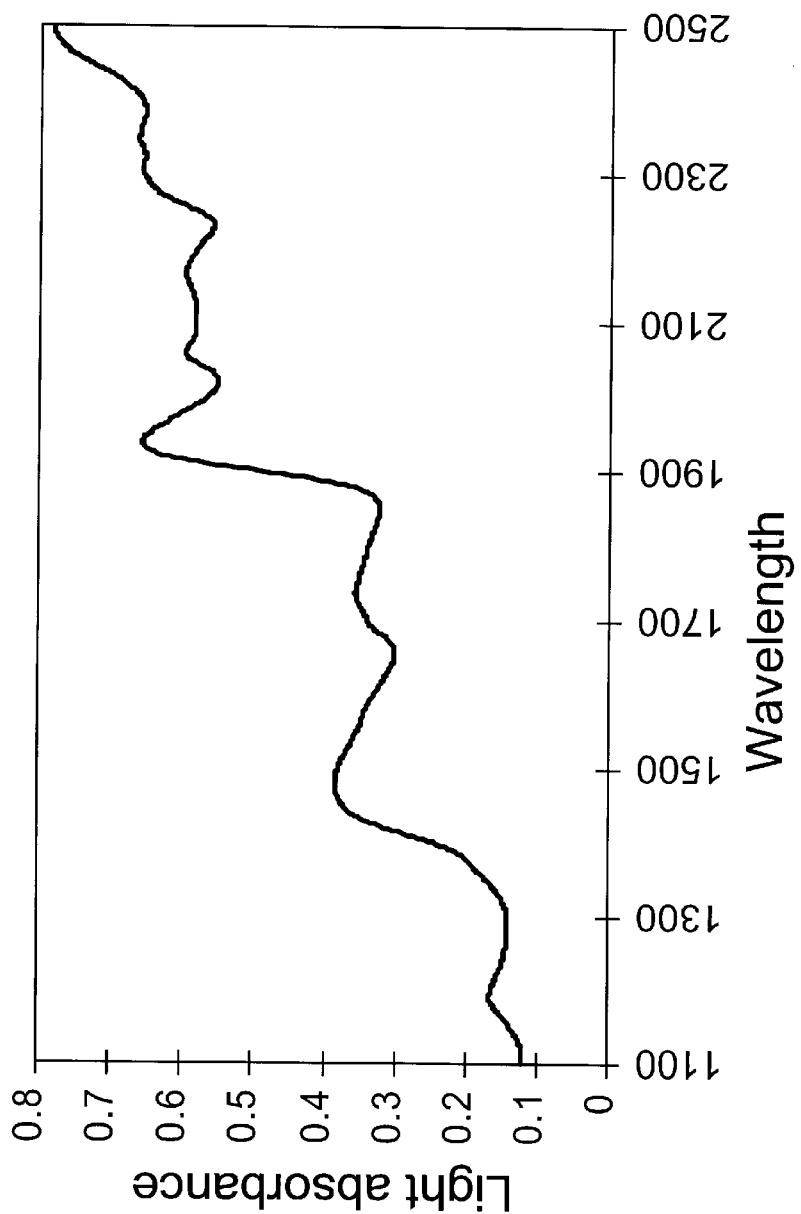
FIG. 12 illustrates an NIRS spectrum of soyabean meal.

By comparing FIGS. 11 and 12, a direct quantification of the soyabean meal composition is difficult because the spectrum of soyabean meal lacks distinguishable peaks, and the spectrum of FIG. 12 is actually a composite spectrum of different substances present in the soyabean meal. Therefore, another way of assessing the amino acid content from the spectrum is to establish the database 221 relating spectra to amino acid content measured by other analysis techniques. The result of the comparison at 219 is, therefore, a nutrient (amino acid) profile 223. This is compared at 225 to the desired profile established by considering the ideal diet for the animal. The batch is then accepted or rejected at step 227 and, if accepted, a nutrient, in this case amino acid additive is added at step 229 to achieve the desired nutrient profile in the feedstuff.

Figure 13:
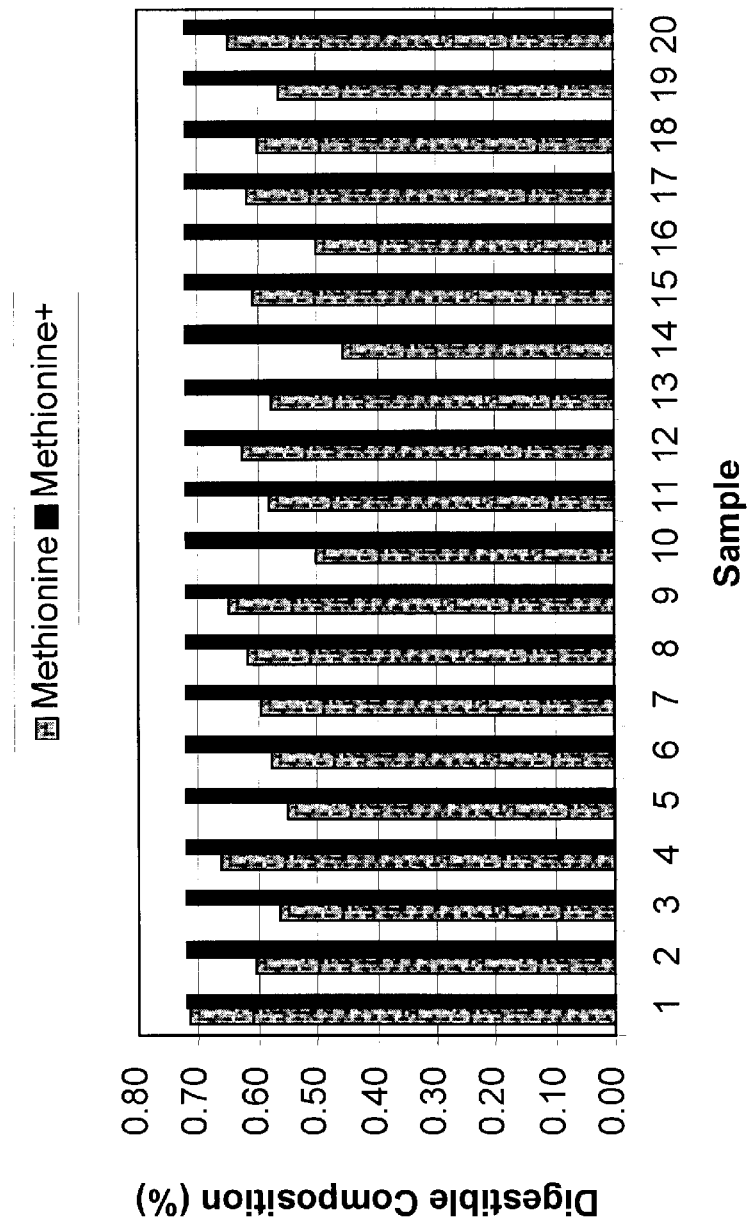
FIG. 13 illustrates levels of digestible methionine in batches of soyabean meal.

FIG. 13 illustrates the level of digestible methionine in the incoming soyabean meal, which can be seen to vary markedly, and the level in the complete feed, i.e. after enhancement by the addition of synthetic methionine. It can be seen that a guaranteed level of 0.74% can be achieved in an embodiment of the invention, compared to the 0.62% average in the raw product.

EXAMPLE 6

Improved Animal Feed

Figure 14:
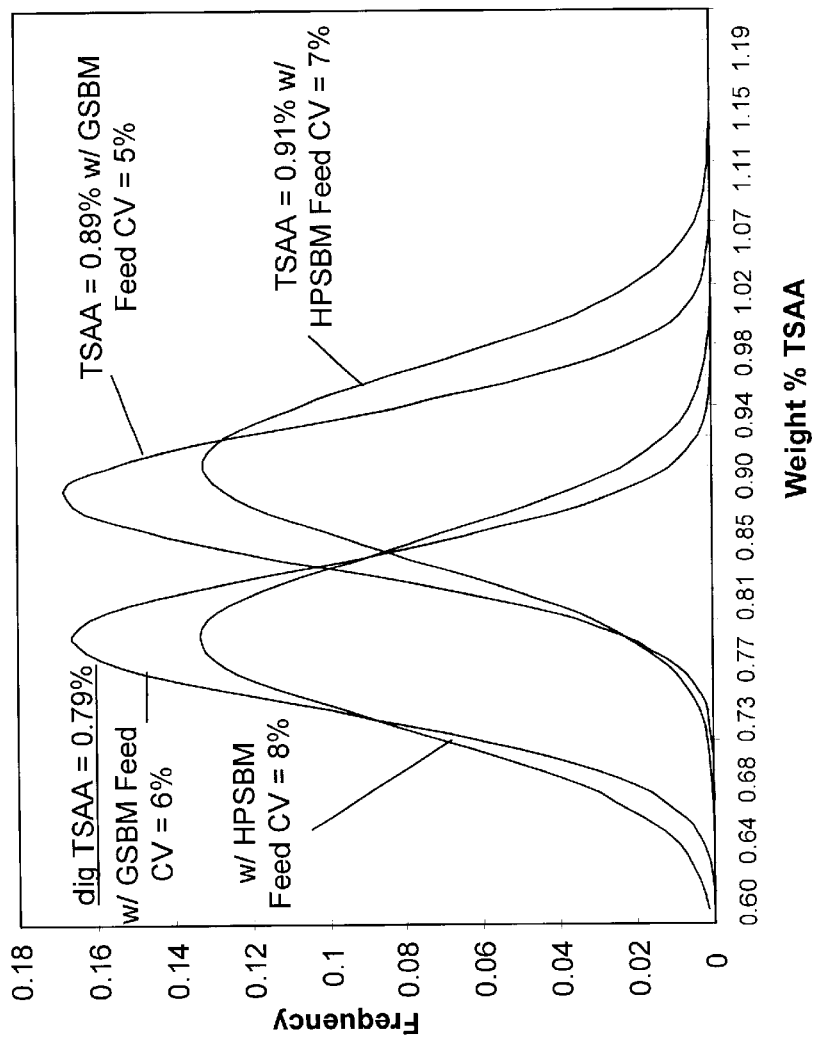
FIG. 14 illustrates levels of total sulfur amino acids ("TSAA") and digestible TSAA in an embodiment of the invention compared to a commercial animal feed.

Use of the improved feedstuffs in animal feeds improves the nutritional and economic value of the feeds. With regard to nutritional value, FIG. 14 illustrates the amounts of TSAA and digestible TSAA in an embodiment of the invention labeled GSBM. The TSAA level in the animal feed of the invention is 0.89% with CV=5%, compared to the known feed containing 0.91% TSAA with CV=7%. Similarly, both animal feeds contain 0.79% digestible TSAA, but the feed of the invention has a lower coefficient of variation.

With regard to economic value of feeds of the invention, Table 2 illustrates the cost savings of using a soyabean meal of the invention "GSBM" in an example animal feed compared to three other animal feeds on the market. The table shows that use of GSBM can reduce the cost of animal feeds by an estimated $0.50 per ton.

TABLE 5

Economic value of feedstuff of the invention in animal feeds

| | AAN Starter | With GSBM | AAN Grower | With GSBM | AAN Finisher | With GSBM |
|---|---|---|---|---|---|---|
| Lysine | 1.19 | 1.16 | 1.05 | 1.02 | 0.95 | 0.93 |
| Methionine | 0.55 | 0.54 | 0.46 | 0.45 | 0.39 | 0.38 |
| TSAA | 0.91 | 0.89 | 0.83 | 0.81 | 0.77 | 0.75 |
| Tryptophan | 0.21 | 0.21 | 0.20 | 0.20 | 0.19 | 0.19 |
| Threonine | 0.76 | 0.76 | 0.70 | 0.70 | 0.66 | 0.66 |
| Price ($/ton) | 149.14 | 148.67 (−0.47) | 146.41 | 145.94 (−0.47) | 144.14 | 143.45 (−0.69) |
| Price ($/ton) w/out Trypto* | 146.72 | 145.63 (−1.09) | 143.04 | 142.39 (−0.65) | 140.53 | 139.93 (−0.60) |

*diets formulated without tryptophan minimum, but minimum protein requirements of 20.7%, 19.4%, and 18.6%

We claim:

1. A method comprising:
   measuring the level of one or more nutrients in batches of a feedstuff;
   determining a target nutrient composition of the feedstuff;
   identifying at least one cluster of one or more batches of the feedstuff;
   determining, for the at least one cluster, an amount of one or more supplemental nutrients needed by the batches in the cluster to reach the target nutrient composition; and
   determining, for the at least one cluster, an economic advantage to supplementing the batches in the cluster with the one or more supplemental nutrients.

2. A method as claimed in claim 1, which further comprises separating the batches in the at least one cluster from batches not in the cluster and combining the batches in the at least one cluster.

3. A method as claimed in claim 2, which further comprises supplementing the batches in the at least one cluster with the one or more supplemental nutrients.

4. A method as claimed in claim 3, which comprises supplementing the batches in the at least one cluster with two or more, or three or more, or four or more supplemental nutrients.

5. A method as claimed in claim 4, which comprises supplementing the batches in the at least one cluster with two or three or four supplemental nutrients.

6. A method as claimed in claim 3, wherein the supplemented batches contain a lower coefficient of variation in the level of a nutrient compared to the coefficient of variation of the nutrient in the starting batches.

7. A method as claimed in claim 1, wherein the feedstuff is byproducts suitable for use in animal feed.

8. A method as claimed in claim 1, which comprises measuring the level of the one or more nutrients using near infrared reflectance spectroscopy.

9. A method as claimed in claim 1, which comprises measuring the level of the total amino acid or acids, digestible amino acid or acids, and protein content of the batches.

10. A method as claimed in claim 9, which comprises measuring the level of the total, digestible, or both the total and digestible content of methionine, lysine, threonine, tryptophane or combinations of those nutrients of the batches.

11. A method as claimed in claim 10, which comprises measuring the level of the total, digestible, or both the total and digestible content of methionine, lysine, or both methionine and lysine in the batches.

12. A method as claimed in claim 1, which comprises measuring one or more of the fat, oil, caloric, fiber, carbohydrate, vitamin and mineral levels in the batches.

13. A method as claimed in claim 12, which comprises measuring the level of calcium, phosphorous, or both calcium and phosphorous in the batches.

14. A method as claimed in claim 1, which comprises measuring two or more, three or more, or four or more nutrient levels in the batches.

15. A method as claimed in claim 14, which comprises measuring two or three or four nutrient levels in the batches.

16. A method as claimed in claim 1, which further comprises, during or after measuring the level of the one or more nutrients, evaluating the statistical distribution of the level of the one or more nutrients between the batches.

17. A method as claimed in claim 1, wherein the feedstuff is soyabean meal.

18. A method as claimed in claim 1, wherein the feedstuff is corn.

19. A method as claimed in claim 1, wherein supplementing the batches in the at least one cluster provides the optimum economic advantage compared to supplementing batches in any other cluster with either the same nutrients or any other measured nutrients.

20. A method as claimed in claim 1, which comprises determining a projected reduced coefficient of variation in the level of a nutrient in batches in the at least one cluster, if supplemented, compared to the coefficient of variation of the nutrient in the starting batches.

21. An improved feedstuff made by:
   measuring the level of one or more nutrients in batches of a feedstuff;
   determining a target nutrient composition of the feedstuff;
   identifying at least one cluster of one or more batches of the feedstuff;
   determining, for the at least one cluster, an amount of one or more supplemental nutrients needed by the batches in the cluster to reach the target nutrient composition;
   determining, for the at least one cluster, an economic advantage to supplementing the batches in the cluster with the one or more supplemental nutrients;
   separating the batches in the at least one cluster from batches not in the cluster and combining them; and
   supplementing the batches in the at least one cluster with the one or more supplemental nutrients to obtain the improved feedstuff.

22. An improved feedstuff as claimed in claim 21, which further comprises, during or after measuring the level of the one or more nutrients, evaluating the statistical distribution of the level of the one or more nutrients between the batches.

23. An improved feedstuff as claimed in claim 21, wherein the coefficient of variation of the one or more nutrients whose level was measured is 5%, 4%, or 3%.

24. An improved feedstuff as claimed in claim 21, wherein the coefficient of variation of the one or more supplemented nutrients is 5%, 4%, or 3%.

25. An animal feed, which comprises an improved feedstuff as claimed in claim 21.

26. An animal feed as claimed in claim 25, wherein the coefficient of variation of the one or more nutrients whose level was measured is 6%, 5%, 4% or 3%.

27. An animal feed as claimed in claim 25, wherein the coefficient of variation of the one or more supplemented nutrients is 6%, 5%, 4% or 3%.

28. A method of feeding an animal, which comprises feeding the animal an animal feed as claimed in claim 25.

29. A method as claimed in claim 28, wherein the animal is a cow, a chicken, a pig, or a sheep.

30. A feasibility method comprising:
   measuring the level of one or more nutrients in a fraction of a total number of batches of a feedstuff;
   determining a target nutrient composition of the feedstuff;
   identifying at least one cluster of one or more batches of the feedstuff;
   determining at least one projected number of batches, within the total number of batches, expected to fall within the at least one cluster;
   determining, for the at least one projected number of batches, the amount of one or more supplemental nutrients needed by the batches to reach the target nutrient composition; and
   determining, for at the least one projected number of batches, an economic advantage to supplementing the batches with the one or more supplemental nutrients.

31. A feasibility method as claimed in claim 30, which further comprises, during or after measuring the level of the one or more nutrients, evaluating the statistical distribution of the level of the one or more nutrients between the batches.

32. A production method, comprising:
   performing the feasibility method as claimed in claim 30;
   measuring the nutritional composition of batches of feedstuff within the total number of batches;
   rejecting any batches that would not fall within the at least one projected number of batches;
   accepting any batches that would fall within the at least one projected number of batches;
   separating the accepted batches from the rejected batches and combining the accepted batches; and
   supplementing the accepted batches with the determined supplemental nutrient amount.

33. A method as claimed in claim 1, which further comprises
   identifying one or more further clusters of one or more batches of the feedstuff;
   determining, for the one or more further clusters, an amount of one or more supplemental nutrients needed by the batches in the cluster to reach the target nutrient composition;
   determining, for the one or more further clusters, an economic advantage to supplementing the batches in the cluster with the one or more supplemental nutrients; and
   identifying, from all clusters for which an economic advantage is determined, the cluster that offers the optimum economic advantage.

34. A method as claimed in claim 33, wherein the economic advantage is measured by profit to the manufacture of the feedstuff for use in an animal feed in light of any variable and fixed costs associated with the manufacture of the feedstuff.

* * * * *